US008537354B2

(12) United States Patent
Maier et al.

(10) Patent No.: US 8,537,354 B2
(45) Date of Patent: Sep. 17, 2013

(54) SYSTEM AND METHOD FOR INSTRUMENT RESPONSE CORRECTION BASED ON INDEPENDENT MEASUREMENT OF THE SAMPLE

(75) Inventors: John Maier, Pittsburgh, PA (US); Michael Fuhrman, Pittsburgh, PA (US)

(73) Assignee: ChemImage Technologies, LLC, Pittsburgh, PA (US)

( * ) Notice: Subject to any disclaimer, the term of this patent is extended or adjusted under 35 U.S.C. 154(b) by 270 days.

(21) Appl. No.: 12/931,868

(22) Filed: Feb. 11, 2011

(65) Prior Publication Data

US 2011/0211763 A1 Sep. 1, 2011

Related U.S. Application Data

(63) Continuation-in-part of application No. 11/831,088, filed on Jul. 31, 2007, now abandoned, and a continuation-in-part of application No. 11/900,169, filed on Sep. 10, 2007, now abandoned.

(60) Provisional application No. 61/303,814, filed on Feb. 12, 2010, provisional application No. 61/324,963, filed on Apr. 16, 2010, provisional application No. 61/434,034, filed on Jan. 19, 2011, provisional application No. 61/460,816, filed on Jan. 7, 2011, provisional application No. 61/403,141, filed on Sep. 10, 2010.

(51) Int. Cl.
*G01J 3/44* (2006.01)
(52) U.S. Cl.
USPC .................................................... 356/301

(58) Field of Classification Search
USPC .............. 356/72–73, 301, 300, 326, 328, 334
See application file for complete search history.

(56) References Cited

U.S. PATENT DOCUMENTS

| 5,113,275 | A | 5/1992 | Patel |
| 5,247,378 | A | 9/1993 | Miller |
| 5,568,286 | A | 10/1996 | Riza |
| 5,850,623 | A | 12/1998 | Carman |
| 6,353,656 | B1 | 3/2002 | LeVert |
| 6,403,947 | B1 | 6/2002 | Hoyt |
| 6,765,668 | B2 | 7/2004 | Gardner, Jr. et al. |

(Continued)

OTHER PUBLICATIONS

May, Willie E. et al, National Institute of Standards & Technology, Certificate of Analysis, Standard Reference material, Relative Intensity Correction Standard for Raman Spectroscopy, 532 nm excitation, certificate issue dated Jan. 28, 2004, pp. 1-6.

(Continued)

*Primary Examiner* — Tarifur Chowdhury
*Assistant Examiner* — Abdullahi Nur

(57) ABSTRACT

A system and method for providing an instrument response correction. A sample is illuminated to generate a first plurality and a second plurality of interacted photons. The first plurality of interacted photons may be detected by a dispersive spectrometer to generate a reference spectrum representative of the sample. The second plurality of interacted photons may be passed through a tunable filter and detected using an imaging detector to generate at least one hyperspectral image. This hyperspectral image may comprise a Raman hyperspectral image or an infrared hyperspectral image. A system may comprise an illumination source, a collection optics, a dispersive spectrometer, a fiber optic, a tunable filter, and an imaging detector.

27 Claims, 12 Drawing Sheets

(56) References Cited

U.S. PATENT DOCUMENTS

| | | | |
|---|---|---|---|
| 6,801,310 B2 | 10/2004 | Kewitsch | |
| 2001/0052979 A1* | 12/2001 | Treado et al. | 356/326 |
| 2003/0135122 A1* | 7/2003 | Bambot et al. | 600/476 |
| 2008/0034833 A1 | 2/2008 | Maier | |
| 2008/0062353 A1 | 3/2008 | Wang | |

OTHER PUBLICATIONS

Choquette, Steve, 2009 USP Annual Scientific Meeting, "Spectral Identification," Sep. 22, 2009.

Choquette, S.J, "Standard Reference Materials for Relative Intensity Correction of Raman Spectrometers," American Laboratory, abstract, May 9, 2011.

International Search Report, PCT/US2007/019688.

* cited by examiner

Figure 7A

MCF SWIR Gen 1 - MCF1000-001

| Temperature (°C) | 1000nm | Transmittance (%)* 1300nm | 1600nm |
|---|---|---|---|
| 15 | 20.044 | 17.196 | 13.036 |
| 17 | 20.261 | 17.076 | 12.986 |
| 20 | 19.743 | 17.802 | 13.072 |
| 22 | 19.854 | 18.305 | 12.717 |
| 25 | 19.251 | 18.221 | 12.664 |
| 27 | 19.340 | 18.296 | 12.657 |
| 30 | 20.295 | 18.323 | 12.894 |
| 32 | 20.615 | 18.113 | 13.126 |
| 35 | 20.020 | 17.264 | 12.867 |
| 37 | 19.758 | 17.323 | 12.401 |
| 40 | 19.658 | 17.500 | 11.930 |
| 42 | 19.935 | 17.651 | 11.786 |
| 45 | 19.388 | 16.448 | 11.184 |

*: Transmittance with Temperature Compensation

| MCF Raman - MCF1500-001 | | | |
|---|---|---|---|
| | Transmittance (%) * | | |
| Temperature (°C) | 520nm | 580nm | 640nm |
| 22 | 12.040 | 17.530 | 19.360 |
| 25 | 11.860 | 17.080 | 20.270 |
| 27 | 12.020 | 16.860 | 20.420 |
| 30 | 10.090 | 14.540 | 17.090 |
| 32 | 10.210 | 15.740 | 18.690 |
| 35 | 10.530 | 15.460 | 16.750 |
| 37 | 10.628 | 16.000 | 16.470 |
| 40 | 12.540 | 17.130 | 18.950 |

| MCF Raman - MCF1500-001 | | | |
|---|---|---|---|
| | Transmittance (%) ** | | |
| Temperature (°C) | 520nm | 580nm | 640nm |
| 22 | 12.040 | 17.530 | 19.360 |
| 25 | 11.670 | 16.020 | 18.330 |
| 27 | 9.150 | 12.850 | 15.120 |
| 30 | 6.048 | 8.033 | 10.160 |
| 32 | 2.883 | 4.473 | 6.125 |
| 35 | 1.322 | 2.071 | 3.856 |
| 37 | 0.978 | 0.981 | 1.891 |
| 40 | 0.373 | 0.491 | 1.124 |

\* : Transmittance with Temperature Compensation

\*\* : Transmittance without Temperature Compensation

Figure 8A

SYSTEM AND METHOD FOR INSTRUMENT RESPONSE CORRECTION BASED ON INDEPENDENT MEASUREMENT OF THE SAMPLE

RELATED APPLICATIONS

This Application is a continuation-in-part of U.S. patent application Ser. No. 11/831,088, filed on Jul. 31, 2007, entitled "Optical Spectroscopy Instrument Response Correction," and a continuation-in-part of U.S. patent application Ser. No. 11/900,169, filed on Sep. 10, 2007, entitled "Temperature Compensation in Liquid Crystal Tunable Filters." This Application also claims priority under 35 U.S.C. 119(e) to the following U.S. Provisional Patent Applications: No. 61/303,814, filed on Feb. 12, 2010, entitled "System and Method for Calibration of Spectroscopic Systems Which Use Tunable Filters," No. 61/324,963, filed on Apr. 16, 2010, entitled "Short-Wavelength Infrared (SWIR) Multi-Conjugate Liquid Crystal Tunable Filter," No. 61/434,034, filed on Jan. 19, 2011, entitled "VIS-SNIR Multi-Conjugate Tunable Filter," No. 61/460,816, filed on Jan. 7, 2011, entitled "Conformal Filter and Method for Use Thereof," and No. 61/403,141, filed on Sep. 10, 2010, entitled "Systems and Methods for Improving Imaging Technology." These applications are hereby incorporated by reference in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array ("FPA") detectors are typically employed. The choice of FPA detector is governed by the spectroscopic technique employed to characterize the sample of interest. For example, silicon ("Si") charge-coupled device ("CCD") detectors or CMOS detectors are typically employed with visible wavelength fluorescence and Raman spectroscopic imaging systems, while indium gallium arsenide ("InGaAs") FPA detectors are typically employed with near-infrared spectroscopic imaging systems.

Wide-field spectroscopic imaging of a sample can be implemented by collecting spectra over the entire area-encompassing the sample simultaneously using an electronically tunable optical imaging filter such as an acousto-optic tunable filter ("AOTF") or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet ("UV"), visible ("VIS"), near infrared ("NIR"), short-wave infrared ("SWIR"), mid infrared ("MIR") wavelengths, long wave infrared wavelengths ("LWIR"), and to some overlapping ranges. These correspond to wavelengths of approximately 180-380 nm ("UV"), 380-700 nm ("VIS"), 700-2500 nm ("NIR"), 850-1800 nm ("SWIR"), 650-1100 nm ("MWIR"), 400-1100 ("VIS-NIR") and 1200-2450 ("LWIR").

In the case of Raman imaging data the real physical phenomenon being measured is the Raman scattered light emanating from a location in a field-of-view represented by a pixel in a data set. The Raman scattered light passes through a set of imaging optics to a detector. In general the optics are fixed components made of solid materials with stable optical characteristics. In full field-of-view Raman imaging of tissues, one of the optics is a liquid crystal tunable filter spectroscopic imaging element. This is a dynamically tunable narrow bandpass (~0.25 nm FWHM) filter that allows imaging of the same field-of-view at different wavelengths, without moving any optics. The specific advantages an approach based on this hardware are realized in the speed of acquisition and the alignment of images at different wavelengths. A disadvantage of this device is that there can be fluctuations in the transmission efficiency that depend on characteristics such as temperature, atmospheric pressure and humidity. These fluctuations are significantly larger than fluctuations of properties of standard physical optics in the same conditions and manifest themselves in the amount of light that is transmitted, and hence on the amount of Raman scattered light that is recorded at the detector. Because these fluctuations vary with environmental conditions, they manifest themselves differently at different operating conditions.

Due to these fluctuations, an optical instrument operating in a real-life scenario does not have a perfect or ideal performance for all wavelengths of light. This is true at an optical component level, at an optical system level, or both. There exists a need for a system and method to overcome these limitations and provide an accurate and reliable means for determining transmission efficiency as it relates to temperature and other environmental conditions.

SUMMARY OF THE INVENTION

The present disclosure relates to a system and method for correcting instrument response of an optical instrument. More specifically, the present disclosure relates to a system and method for correcting instrument response using an independent system with a known calibration.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure. The patent or application file contains at least one drawing executed in color. Copies of this patent or patent application publication with color drawing(s) will be provided by the Office upon request and payment of the necessary fee.

In the drawings:

FIG. 7A is a data chart representative of an exemplary MCF SWIR filter's transmittance performance with respect to the temperature increment.

FIG. 8A is a data chart representative of an exemplary MCF Raman filter's transmittance performance with respect to the temperature increment.

DETAILED DESCRIPTION

Figure 1A:
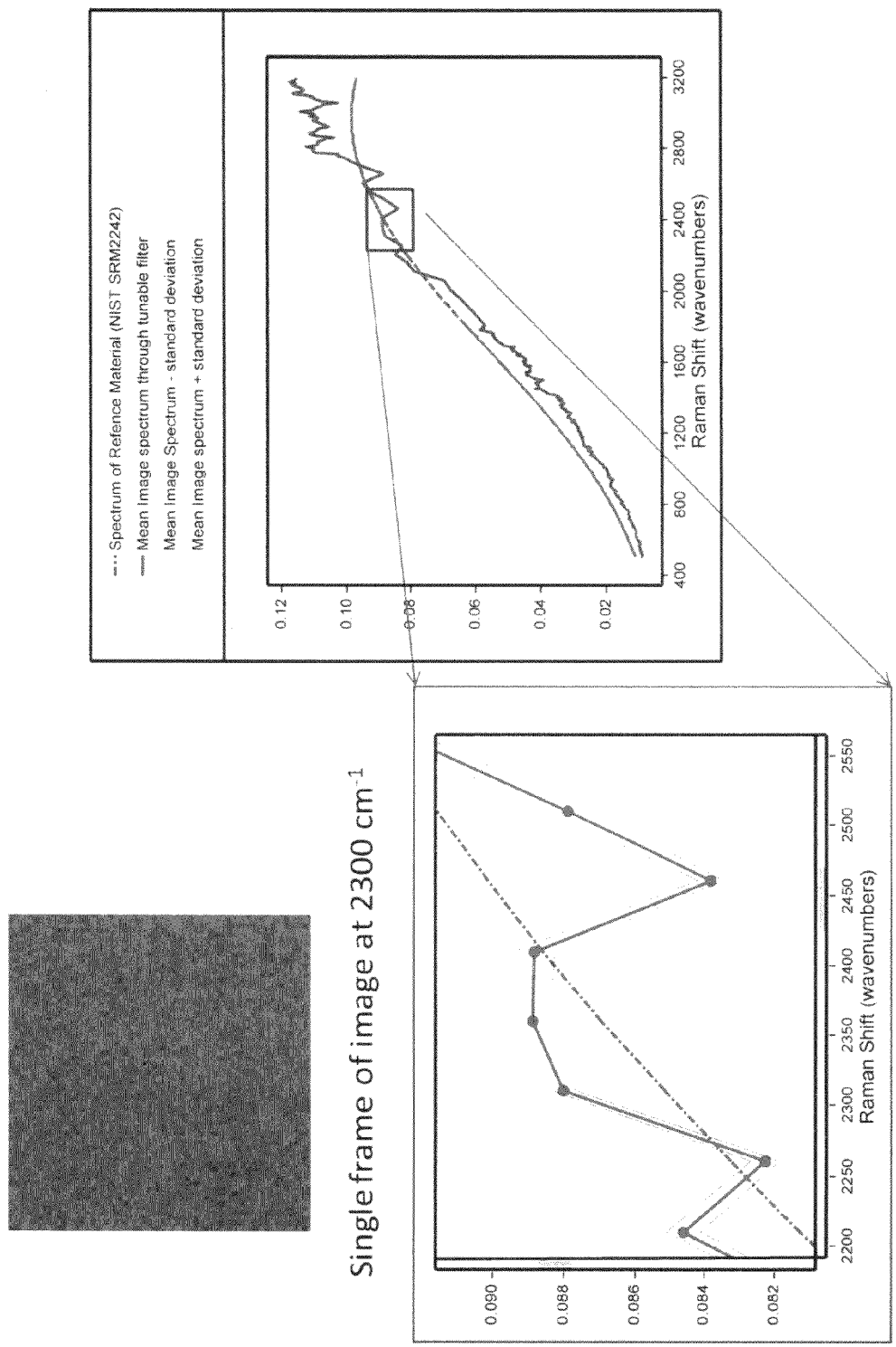
FIG. 1A is illustrative of the wavelength to wavelength variation in transmission of a tunable filter.

Reference will now be made in detail to the preferred embodiments of the present disclosure, examples of which are illustrated in the accompanying drawings. Wherever possible, the same reference numbers will be used throughout the drawings to refer to the same or like parts.

The present disclosure provides for a system and method which hold potential for enabling the evaluation of an imperfect optical component or system in terms of its transmission or detection performance. In the case where the component or system is stable, the present disclosure contemplates that any deviations from the perfect or ideal performance may be measured and accounted for.

If a spectrum of this source were taken with an ideal instrument, the spectrum would be a flat horizontal line as a function of wavelength. In one embodiment, an ideal light source that produces the same number of photons at each wavelength may be used. When this ideal source is used with an imperfect instrument, however, the measured spectrum is not a straight line. The real spectrum obtained from a perfect source with the same number of photons at each wavelength carries information about the instrument response of the real-world, imperfect optical instrument. The instrument response is the spectral response. In general, instrument response as a function of any number of parameters can be measured and corrected for.

In working with optical systems, the presence of the instrument response—i.e., a manifestation of an instrument's imperfections or deviations from the ideal response—is evident in both dispersive and imaging spectroscopy experiments. For example, in case of a dispersive spectroscopy measurement (e.g., measurement of a Raman spectrum) on a sample with some background fluorescence, it is observed that the baseline on which the Raman spectrum sits is not a flat line. The features in the baseline (e.g., its lack of ideal flatness) have a characteristic that is due in part to the optical components and detectors that comprise the system used for the measurement.

Direct measurement of molecules in intact biospecimens holds potential for enabling the evaluation of these samples without the use of antibody-, or gene-based complex biological reagents. Raman molecular imaging ("RMI") may be one technology which holds potential for delivering this molecular information into the context of histopathological evaluation of tissue samples. RMI builds on the demonstrated success of Raman spectroscopy in the analysis of biological samples by integrating full field-of-view digital imaging with high precision spectrally sensitive optics. The system and method of the present disclosure hold potential for optimizing the instrumentation so that it can perform in a stable reproducible fashion to deliver this biological information to the clinicians on a routine basis. The present disclosure also contemplates that infrared imaging may hold similar potential for application in these scenarios.

In particular the application of Raman imaging systems to tissue imaging applications requires a level of accuracy that is significantly higher than the requirement for standard use on relatively high concentration chemicals as in the pharmaceutical industry (where this technology finds its largest user base). The system and method of the present disclosure hold potential for enabling users to routinely apply this technology to tissue analysis, overcoming the limitations of the prior art. The system and method disclosed herein hold potential for delivering information directly from the molecules which comprise a tissue, without reagents, without destroying the sample so that subsequent evaluations can be performed.

Figure 1B:
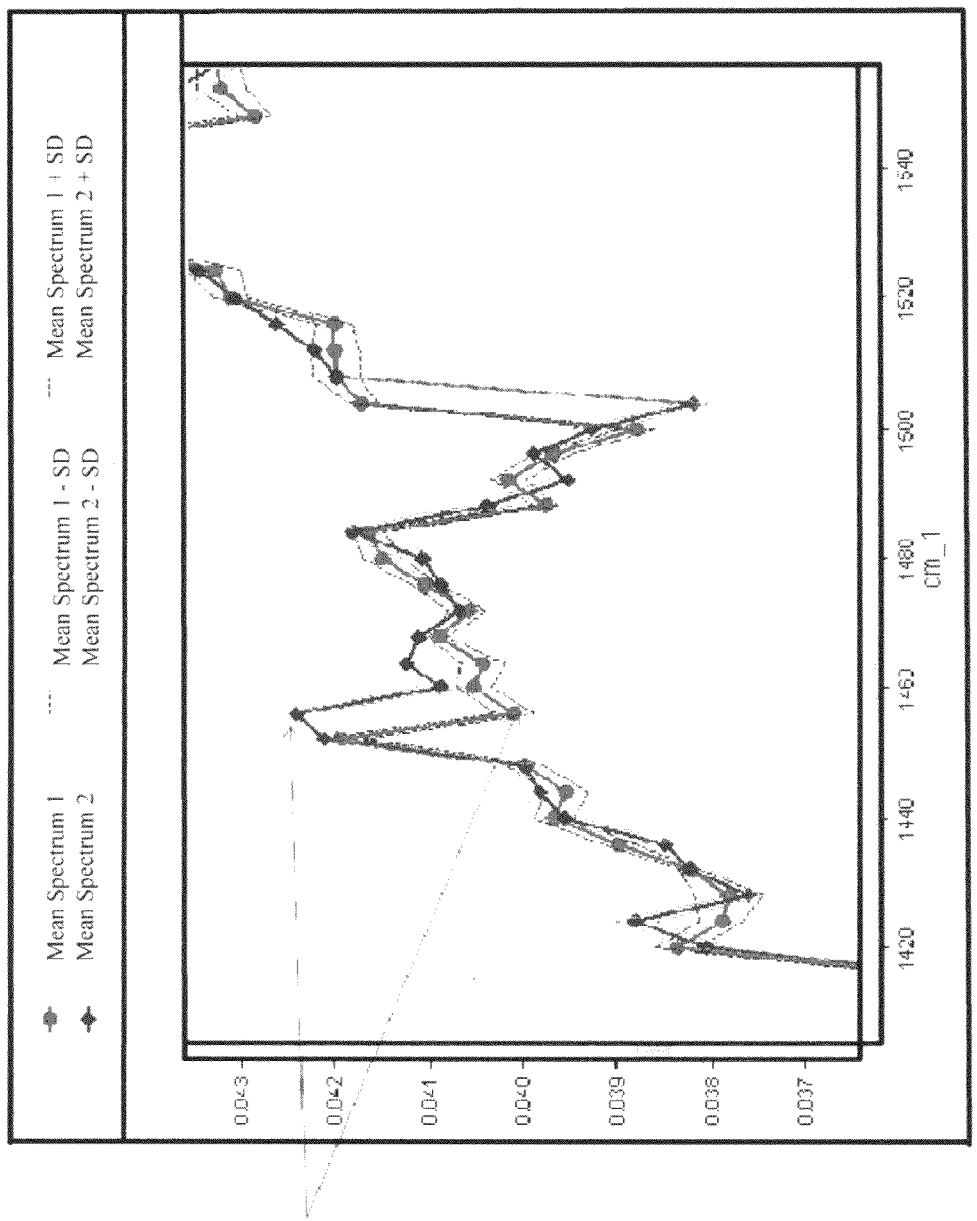
FIG. 1B is illustrative of the variance that occurs in filter transmission over time.

Variations in the transmission of a tunable filter can be demonstrated in a simple experiment by measuring the Raman scattering from a standard material through a liquid crystal tunable filter. The National Institute for Standards and Technology ("NIST") provides a standard reference material (SRM 2242) that has a well characterized spectral response to laser excitation. FIGS. 1A and 1B show a plot of this response with the mean intensity of an image of a piece of this material as a function of Raman shift acquired with a tunable filter-based system. FIG. 1A is illustrative of the wavelength to wavelength variation in the transmission of the tunable filter with the known spectrum of the material (red dashed line). A single frame of the image stack is shown to indicate the level of pixel to pixel to noise. FIG. 1B is illustrative of the detailed spectrum of the same measurement made on the same sample at a different time to indicate the variance that occurs in the filter transmission over time.

The Raman image is acquired over the full Raman scattering spectral range. The image is comprised of a series of 196 frames acquired at different center bandpass settings of the filter. The plot represented in red dashed line is the known spectrum of the material provided by NIST. The red solid line is the intensity of each frame versus center band setpoint. Along with the plot of mean intensity is shown the mean plus and minus the standard deviation of each frame (blue dotted lines). This is included to point out that the variance from frame to frame is not due to the pixel noise of the image (which is indicated by the standard deviations).

The transmission spectrum is not smooth; it has sharp discontinuities and could not be well approximated by an analytic equation. The fundamental reason why these discontinuities exist is related to the operation of liquid crystal tunable filters as a collection of independently functioning liquid crystal elements stacked together.

The tunable filter works by aligning the center bandpass of a series of liquid crystal elements which can each be independently adjusted in terms of a periodic (as a function of wavelength) transmission function. The overall bandpass of the filter is determined by the multiplication of the transmission of each of the elements. In order to select a specific center bandpass for the whole filter, an operating point is chosen for each element of the filter. During the manufacturing process the filter performance is optimized around high center bandpass throughput and high out-of-band light rejection. In order to perform this optimization, operating point choices are made that can lead to very different operating points for a given element at two adjacent wavelength setpoints. Because the choices of operating points are driven by out-of-band rejection, transmission smoothness is sacrificed. This is true about filters from multiple vendors with different designs.

If the transmission function were constant, a simple ratiometric correction would be feasible. Data from a measurement identical to that shown in FIGS. 1A and 1B on the same instrument and sample illustrates how this discontinuous transmission curve changes over time. FIG. 1B illustrates the mean and standard deviation spectra for a second measurement on the same instrument. The assumption here is that of all of the components in the system, the tunable filter is the least stable in terms of behavior over time. This assumption is supported by the clear presence of discontinuities consistent with filter reset points in the spectra shown and the fact that all of the other fixed optics in the system have smooth transmission functions over the relevant wavelength range.

An instrument response correction ("IRC") relates a set of measurable physical properties (the truth) to the output of an instrument (the measurement). In the case of the measurement of Raman scattered light at any wavelength, $\lambda$, there is a simple relationship between the measured intensity and the actual number of photons that are emanating from a sample:

$$R(\lambda)_{Meas} = \alpha(\lambda)_{IRC} \times R(\lambda)_{true}$$

In this case $\alpha_{IRC}$ is a unitless scalar that is essentially the transmission efficiency of the system at the wavelength being studied. Actual measurements are made in the units of output of the CCD camera. For the purposes of the relationship above, the unit conversions are ignored because they do not impact the instrument response correction $R_{Meas}$ and $R_{true}$ should be considered to include such unit conversions that are necessary to move them both into the unit of detector counts.

In one embodiment, the present disclosure provides for a method incorporating the use of the SRM2242 from NIST. Based on the instructions for use the method involves: placing the standard sample in a Raman measurement system, measuring a spectrum of the material on the instrument, calculating an instrument response correction based on the known spectrum and the measured spectrum, using the instrument response correction spectrum to correct subsequent measurements on the system.

This method may hold potential for systems which have a dispersing element and either a linear CCD detector, or some method of scanning the dispersing element as in a scanning monochromator. With measurements based on tunable filter technology the same basic approach may be taken where the measured spectrum is the spectrum at either a single pixel or the mean of spectra acquired at many pixels. Experimental measurements using this methodology may use the available NIST standard as a sample and existing equipment using Raman imaging systems integrating fixed optics and tunable filters from different manufacturers can be surveyed.

In another embodiment, the present disclosure provides for a system and method for determining an instrument response correction by making a second measurement on the sample with an independent measurement system with established calibration.

Dispersing spectrometers are built of fixed optical components with well understood drift and fluctuation due to environmental changes. Because of this established validation a dispersing spectrometer can be used as a plausible reference measurement used to correct measurements made with other devices.

Figure 2:
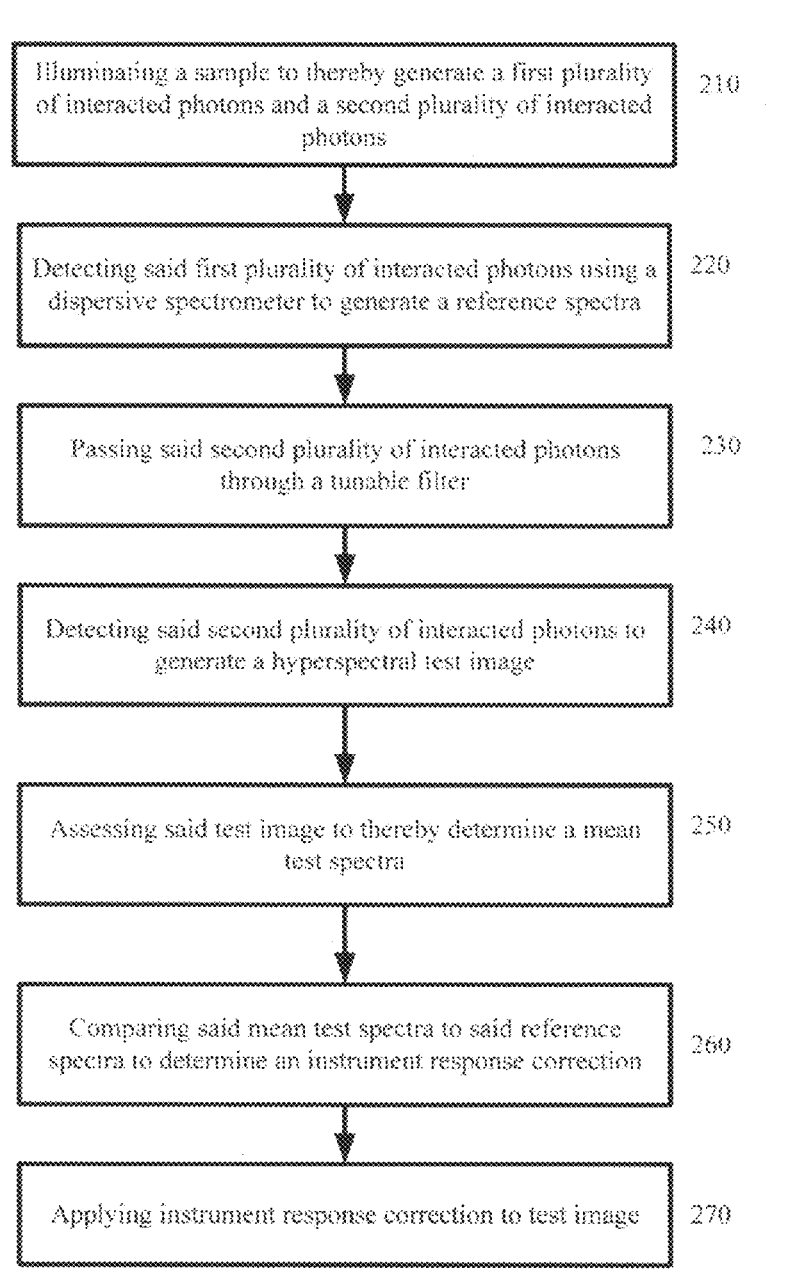
FIG. 2 is representative of a method of the present disclosure.

In one embodiment, the present disclosure contemplates the use of an independent measurement of the sample using a dispersing spectrometer as the true spectrum of the sample as the known reference value. FIG. 2 illustrates one embodiment of the present disclosure. The method, 200, provides or illuminating a sample in step 210 to thereby generate a first plurality of interacted photons and a second plurality of interacted photons. This illumination may be achieved by utilizing at least one of active illumination and passive illumination. In an embodiment comprising active illumination, the illumination may be achieved using a laser light source. In an embodiment utilizing passive illumination, the illumination may be achieved using a solar radiation source. At least one of the first and second pluralities of interacted photons may comprise photons scattered by the sample, reflected by the sample, absorbed by the sample, emitted by the sample, and combinations thereof.

The system and method of the present disclosure hold potential for interrogating a wide variety of samples. In one embodiment, the sample may be a biological sample. In another embodiment, the sample may comprise a chemical sample, an explosive sample, a hazardous sample, a forensic sample, a pharmaceutical sample, and combinations thereof.

A first plurality of interacted photons may be detected using a dispersive spectrometer in step 220 to thereby generate at least one reference spectrum representative of said sample. In one embodiment, these photons may be transmitted to a dispersive spectrometer via a fiber optic. In one embodiment, this fiber optic may comprise a fiber array spectral translator device. This reference spectrum may comprise a Raman reference spectrum, an infrared reference spectrum, and combinations thereof. An infrared spectrum, as contemplated by the present disclosure, may comprise at least one of: a short-wave infrared reference spectrum, a near infrared reference spectrum, a mid-wave infrared spectrum, a long wave infrared spectrum, and combinations thereof. In one embodiment, multiple reference spectra representative of said sample may be obtained using a dispersive spectrometer. These reference spectra may then be assessed to determine a mean reference spectrum.

In step 230 a second plurality of interacted photons may be passed through a tunable filter. In one embodiment, this tunable filter may sequentially filter the second plurality of interacted photons into a plurality of predetermined wavelength bands. In one embodiment, the tunable filter may comprise technology available from ChemImage Corporation, Pittsburgh, Pa. This technology is more fully described in the following U.S. Patents and U.S. Patent Applications, which are hereby incorporated by reference in their entireties: U.S. Pat. No. 6,992,809, issued on Jan. 31, 2006, entitled "Multi-Conjugate Liquid Crystal Tunable Filter"; U.S. Pat. No. 7,362,489, issued on Apr. 22, 2008, also entitled "Multi-Conjugate Liquid Crystal Tunable Filter"; U.S. Provisional Patent Application No. 61/324,963, filed on Apr. 16, 2010, entitled "Short-Wavelength Infrared (SWIR) Multi-Conjugate Liquid Crystal Tunable Filter"; U.S. Provisional Patent Application No. 61/460,816, filed on Jan. 7, 2011, entitled "Conformal Filter and Method for Use Thereof"; and U.S. Provisional Patent Application No. 61/403,141, filed on Sep. 10, 2010, entitled "Systems and Methods for Improving Imaging Technology."

In one embodiment, the tunable filter may comprise a liquid crystal tunable filter, a multi-conjugate liquid-crystal tunable filter, and combinations thereof. Other embodiments of the present disclosure may utilize a device selected from the group consisting of: an acusto-optical tunable filter ("AOTF"), Evans Split-Element liquid crystal tunable filter, Sole liquid crystal tunable filter, Ferroelectric liquid crystal tunable filter, Fabry Perot liquid crystal tunable filter, a hybrid filter, and combinations thereof.

Referring again to FIG. 2, the method 200 provides for detecting a second plurality of interacted photons in step 240. This detection 240 may be accomplished using an imaging detector and generate at least one hyperspectral test image representative of the sample. In one embodiment, this hyperspectral test image may comprise at least one of: a Raman hyperspectral image, an infrared hyperspectral image, and combinations thereof. This infrared hyperspectral image may be selected from the group consisting of: a short-wave infrared hyperspectral image, a near infrared hyperspectral image, a mid-wave infrared hyperspectral image, a long-wave infrared hyperspectral image, and combinations thereof.

In one embodiment, the method 200 may detect said first and second plurality of photons substantially simultaneously. This embodiment holds potential for providing active feedback during operation. In another embodiment, the method 200 may detect said first and second plurality of photons sequentially.

In step 250, a hyperspectral test image may be assessed to thereby determine a mean test spectrum. This mean test spectrum may be representative of the mean intensity of a plurality of pixels in said hyperspectral test image. The mean test spectrum may be compared to a reference spectrum in step 260 to determine an instrument response correction. This comparison may be achieved by applying one or more chemometric techniques. Such techniques may include, but are not limited to, the following: principal component analysis ("PCA"), multivariate curve resolution ("MCR"), partial least squares discriminant analysis ("PLSDA"), k means clustering, band t. entropy method, adaptive subspace detector, cosine correlation analysis ("CCA"), Euclidian distance analysis ("EDA"), partial least squares regression ("PLSR"), spectral mixture resolution ("SMR"), a spectral angle mapper metric, a spectral information divergence metric, a Mahalanobis distance metric, a spectral unmixing algorithm, and combinations thereof. A spectral unmixing metric is disclosed in U.S. Pat. No. 7,072,770 entitled "Method for Identifying Components of a Mixture via Spectral Analysis," which is hereby incorporated by reference in its entirety. In step 270 an instrument response correction may be applied to said hyperspectral test image.

Application of an instrument response correction 270 may result in an adjusted mean test spectrum associated with the test image. This adjusted mean test spectrum may be substantially equal to the reference spectrum obtained in step 220.

In one embodiment, the method 200 may further comprise masking a hyperspectral test image. In such an embodiment, the mask may be such as to include those pixels sampled by said dispersive spectrometer and exclude those pixels not sampled by said dispersive spectrometer.

The base assumption is that the mean spectrum of the imaged area measured from a dispersive spectrometer should match the mean spectrum from the image acquired of the same area through the tunable filter. This type of measurement is feasible because the tunable filter only uses one polarization of the light emanating from the sample. Light with the unused polarization can be sent to a dispersing spectrometer and simultaneously measured to provide the reference spectrum. Key considerations relevant to this approach are: 1) to ensure that light collected with each polarization will have the same spectral distribution, 2) to ensure that spatial sampling and detection efficiency are matched for both arms of the measurement system, 3) to ensure that any sample changes during the course of the image based measurement are captured in the parallel dispersive spectrometer based measurement. This may be accomplished by masking the image of the sample to include only those pixels which are sampled by the dispersive spectrometer and acquiring multiple dispersive spectra which are combined to provide a synthesized reference spectrum which most accurately reflects what the image spectrum should be.

Figure 3A:
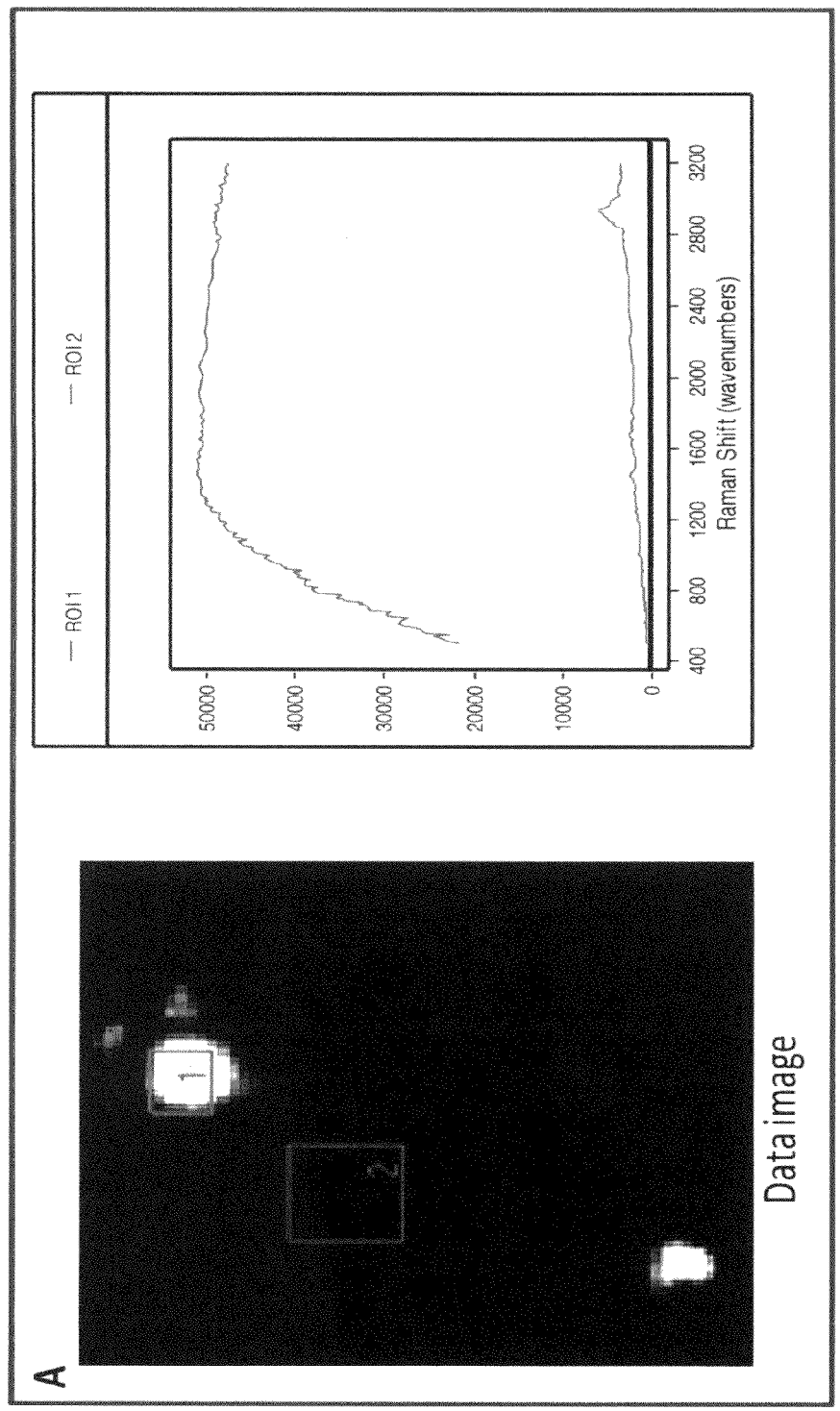
FIG. 3A illustrates an image and associated spectra for regions of a sample.
Figure 3B:
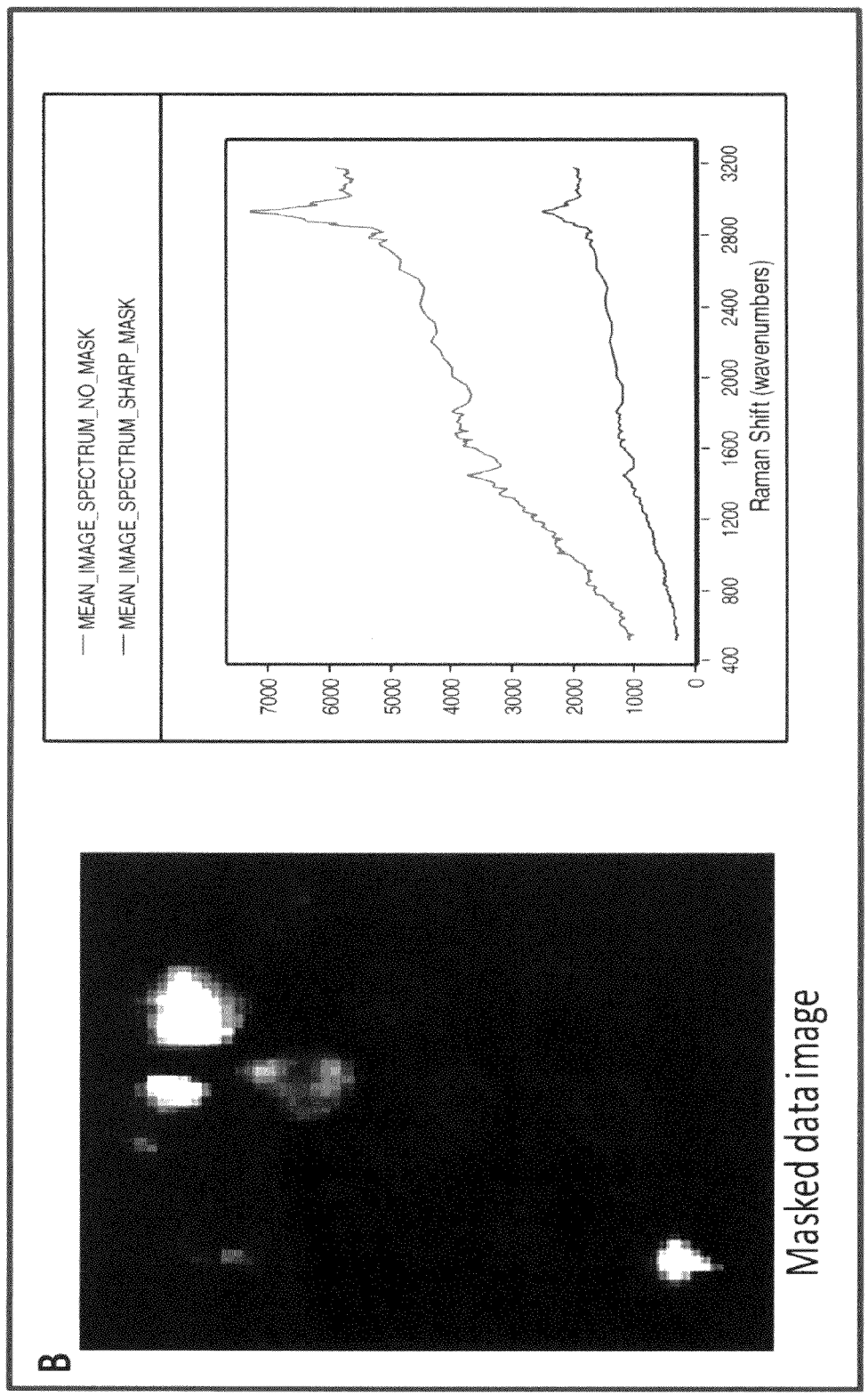
FIG. 3B illustrates the same field of view as FIG. 3A after masking for pixels sampled by a dispersive spectrometer.

FIGS. 3A and 3B illustrate both a typical mask of where fibers sample a field of view of a microscope and the variation in spectral of some localized components of tissue which photobleach or photodegrade during the image acquisition. FIG. 3A illustrates an image and spectra from a Raman image of tissue. The spectra shown are from the two locations in the image indicating typical tissue signature 310 and localized fluorescent object 320. FIG. 3B illustrates the same field of view after masking for the pixels sampled by a dispersive spectrometer. The spectra shown are the mean spectrum of the image before 330 and after 340 the masking.

Figure 4:
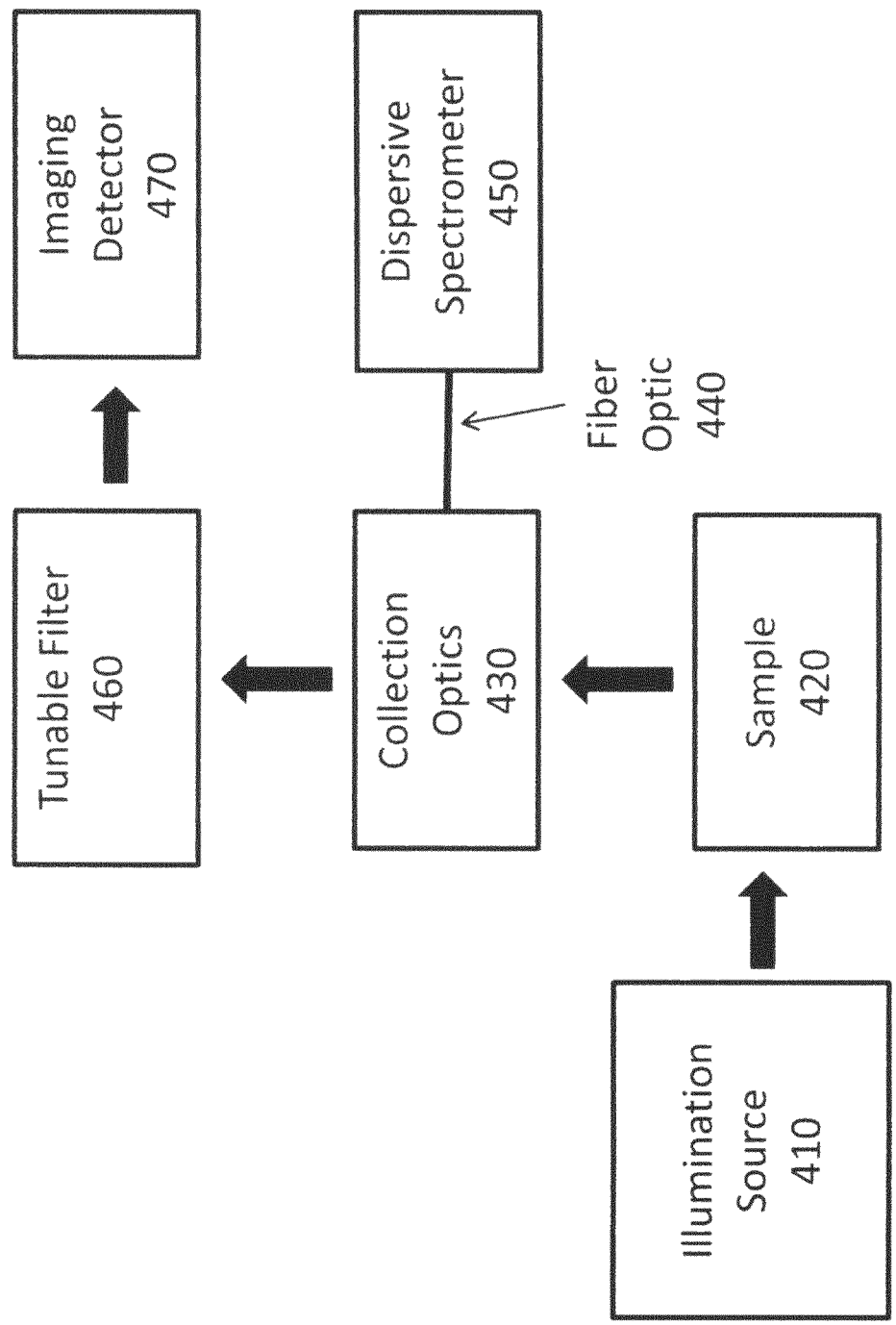
FIG. 4 is illustrative of a system of the present disclosure.

The present disclosure also provides for a system, illustrated by FIG. 4. The system 400 may comprise an illumination source 410 configured to illuminate a sample 420 to thereby generate a first plurality of interacted photons and a second plurality of interacted photons. In one embodiment, the system may comprise a platform for holding the sample. These interacted photons may be collected using collection optics 430. A first plurality of interacted photons may be transmitted to a dispersive spectrometer 450 via a fiber optic 440, which may comprise a fiber array spectral translator device ("FAST"). FAST technology may comprise technology available from ChemImage Corporation, Pittsburgh, Pa. A second plurality of interacted photons may be passed through a tunable filter 460. This tunable filter 460 may comprise a liquid crystal tunable filter, a multi-conjugate liquid crystal tunable filter, and combinations thereof. The tunable filter 460 may also comprise an acusto-optical tunable filter ("AOTF"), Evans Split-Element liquid crystal tunable filter, Solc liquid crystal tunable filter, Ferroelectric liquid crystal tunable filter, Fabry Perot liquid crystal tunable filter, a hybrid filter, and combinations thereof. The tunable filter 460 may be configured so as to sequentially filter interacted photons into a plurality of predetermined wavelength bands.

An imaging detector 470 may be configured so as to detect a second plurality of interacted photons and generate at least one hyperspectral test image. An imaging detector 470 may comprise a Raman hyperspectral imaging detector, an infrared hyperspectral imaging detector, and combinations thereof. An infrared hyperspectral imaging detector may comprise at least one of: a short-wave infrared hyperspectral imaging detector, a near infrared hyperspectral imaging detector, a mid-wave infrared hyperspectral imaging detector, a long wave hyperspectral imaging detector, and combinations thereof.

Imaging detector 470 may comprise a detector selected from the group consisting of: a CCD detector, an ICCD detector, an InGaAs detector, an extended range InGaAs detector, an InSb detector, a PtSi detector, a CMOS detector, a MCT detector, an intervac-intensified detector, a microbolometer, and combinations thereof.

The system 400 may also be configured to operate in conjunction with one or more processors. In one embodiment, this processor may be configured so as to generate a mean spectrum representative of a hyperspectral test image, compare a mean spectrum to a reference spectrum, determine an instrument response correction, and apply an instrument response correction to a hyperspectral image.

The present disclosure also provides for a data storage medium containing program code, which when executed by a processor causes the processor to: illuminate a sample to generate a first plurality of interacted photons and a second plurality of interacted photons, detect a first plurality of interacted photons using a dispersive spectrometer to thereby generate a reference spectrum representative of a sample, pass a second plurality of interacted photons through a tunable filter, detect a second plurality of interacted photons using an imaging detector to thereby generate at least one hyperspectral test image, assess said hyperspectral test image to thereby determine a mean test spectrum wherein said mean test spectrum is representative of the mean intensity at each pixel in said hyperspectral test image, compare said mean test spectrum to a reference spectrum to thereby determine an instrument response correction, and apply said instrument response correction to said hyperspectral test image.

The data storage medium, when executed by a processor may further cause the processor to obtain a plurality of reference spectra representative of a sample via said dispersive spectrometer and assess said plurality of reference spectra to thereby determine a mean reference spectrum representative of the sample. In another embodiment, the processor may further mask a hyperspectral test image so as to include a first plurality of pixels sampled by said dispersive spectrometer and exclude a second plurality of pixels not sampled by said dispersive spectrometer.

The present discourse also provides for a method for correcting for instrument response by having the instrument actively report its current status and correct the data during acquisition. This is possible in the case where a user has access to fundamental data acquired during the manufacturing of the filter and the ability to use that information during operation of a filter. Such interaction holds potential for enabling modification to the communication to and from the filter in a way that holds potential for instrument response correction.

In one embodiment, a filter control system may use a lookup table stored in memory to determine the proper set of control voltages for the stages that comprise the filter. This table may comprise a set of voltages for each possible bandpass center setpoint and operating temperature. When the filter is sent the command to tune to a specific bandpass center, the controller may query the temperature of the filter, refer to the lookup table to determine the appropriate control voltages for the temperature and center bandpass, then apply the appropriate voltage to each stage of the filter. To implement this method the controller may be modified to report the estimated transmission of the filter for the center bandpass and operating temperature.

The present disclosure compensates a system and method to correct for variations in filter transmission. In one embodiment, this variation can be corrected at the filter controller level by changing the code in the filter controller software to read and report appropriate transmission values from an augmented data lookup table. This may also involve a change in the lookup table data structure and in the communication protocols between the filter and the software that controls the rest of data acquisition. An alternative approach is to generate a second lookup table to provide a transmission correction factor for each bandpass center value and temperature. Software external to the filter controller software could independently read values from this file and apply corrections as needed to the raw data after it is collected from the camera.

Both embodiments may implement parallel data recording of both the raw data and the corrected data.

Another alternative embodiment may comprise developing a lookup table for instrument transmission characteristics for the whole system based at measurements on a NIST standard at each bandpass setting and operating temperature. This could be implemented as described in the alternative approach above. This may involve a measurement that carefully explored the operating space of the filter in terms of temperature and center bandpass. Two possible embodiments of such a method are provided for herein. In one embodiment, the present disclosure provides for a method comprising: measuring or calculating the transmission over the operational wavelength range of each stage of the tunable filter at each environmental operating point (one or more of: temperature, humidity, atmospheric pressure), and at each set point for centerbandpass; determining parameters that report performance of the assembled filter in each operating state from the measured or calculated transmission data (state includes center bandpass, environmental conditions as listed above); performing the following: peak transmission, full width half maximum of transmission band, and area under transmission band, integrated out of band signal; creating a lookup table of one or more performance parameters (listed above) that is either: loaded into the filter control microprocessor memory or recorded in a data file stored in memory or media associated with the system in which the filter is integrated; and implementing a control software that sets the filter in response to some external electronic command and reports back to the software sending the external command the desired performance parameters through some communication mechanism and or protocol. In one embodiment, the method may further comprise integrating out of band signal in spectral ranges limited to where detectors are sensitive can be performed.

Figure 5:
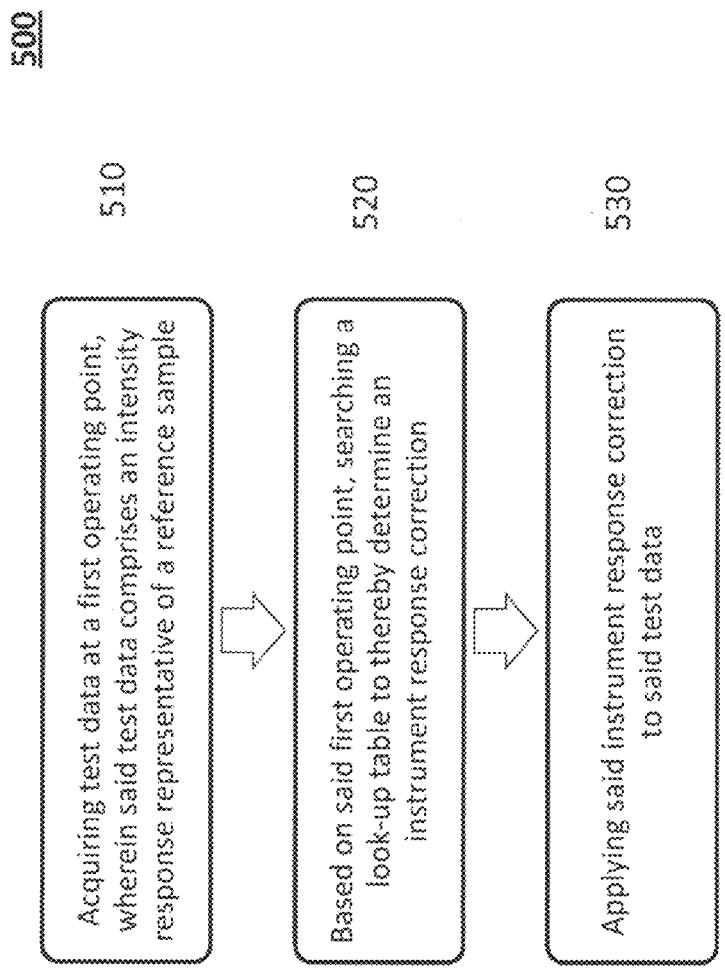
FIG. 5 is representative of a method of the present disclosure.

Another embodiment may comprise: measuring or calculating the transmission of the assembled filter stages at each environmental operating point and centerbandpass setpoint; determining parameters that report performance of the assembled filter in each operating state from the measured or calculated transmission data (state includes center bandpass, environmental conditions as listed above); performing the following: peak transmission, full width half maximum of transmission band, and area under transmission band, integrated out of band signal; creating a lookup table of one or more performance parameters (listed above) that is either: loaded into the filter control microprocessor memory or recorded in a data file stored in memory or media associated with the system in which the filter is integrated; and implementing a control software that sets the filter in response to some external electronic command and reports back to the software sending the external command the desired performance parameters through some communication mechanism and/or protocol. In one embodiment, the method may further comprise integrating The present disclosure also provides for a method, illustrated by FIG. 5, for filter modification based on transmission efficiency. The method 500 provides for acquiring test data at a first operating point in step 510 wherein said test data comprises an intensity response representative of a reference sample. In one embodiment, the method 500 may further comprise acquiring said test data by illumination a reference sample to thereby generate a plurality of interacted photons, passing said plurality of interacted photons through a tunable filter, and detecting said plurality of interacted photons to thereby generate test data representative of said sample.

In one embodiment, the tunable filter may comprise a liquid crystal tunable filter, a multi-conjugate liquid-crystal tunable filter, and combinations thereof. Other embodiments of the present disclosure may utilize a device selected from the group consisting of: an acusto-optical tunable filter ("AOTF"), Evans Split-Element liquid crystal tunable filter, Solc liquid crystal tunable filter, Ferroelectric liquid crystal tunable filter, Fabry Perot liquid crystal tunable filter, a hybrid filter, and combinations thereof.

In one embodiment, this test data may comprise at least one of Raman test data, infrared test data, and combinations thereof. Infrared test data may comprise at least one of: short wave infrared test data, near infrared test data, mid wave infrared test data, long wave infrared test data, and combinations thereof. Test data may comprise one or more hyperspectral images. In one embodiment, the test data may comprise at least one of: a Raman hyperspectral image, an infrared hyperspectral image, and combinations thereof. An infrared hyperspectral image may comprise at least one of: a short wave infrared hyperspectral image, a near infrared hyperspectral image, a mid wave infrared hyperspectral image, a long wave infrared hyperspectral image, and combinations thereof.

In step 520 a look-up table may be searched based on an operating point to thereby determine an instrument response correction. In one embodiment, the look-up table may comprise a plurality of instrument response corrections, wherein each instrument response correction corresponds to an intensity response representative of said reference sample at an operating point. This operating point may comprise an environmental operating point such as a temperature, a humidity, an atmospheric pressure, and combinations thereof. In one embodiment, the method 500 may further comprise constructing one or more look-up tables by operating a system to thereby record an intensity response representative of a reference sample at each of a plurality of operating points. In step 530 an instrument response correction may be applied to test data.

The present disclosure also provides for a data storage medium containing program code, which when executed by a processor causes said processor to perform the following: acquire test data at a first operating point, wherein said test data comprises an intensity response representative of a reference sample; based on said first operating point, search a look-up table to thereby determine an instrument response correction, wherein said look-up table comprises a plurality of instrument response corrections, and wherein each instrument response correction corresponds to an intensity response representative of said reference sample at an operating point; and apply said instrument response correction to said test data.

In one embodiment, the data storage medium may further cause the processor to construct at least one look-up table. This may be achieved by operating a system to thereby record an intensity response representative of a reference sample at each of a plurality of operating points. This test data may be acquired by causing the processor to illuminate a reference sample to thereby generate a plurality of interacted photons, pass said interacted photons through a tunable filter, and detect said plurality of interacted photons to thereby generate test data representative of said reference sample.

Figure 6:
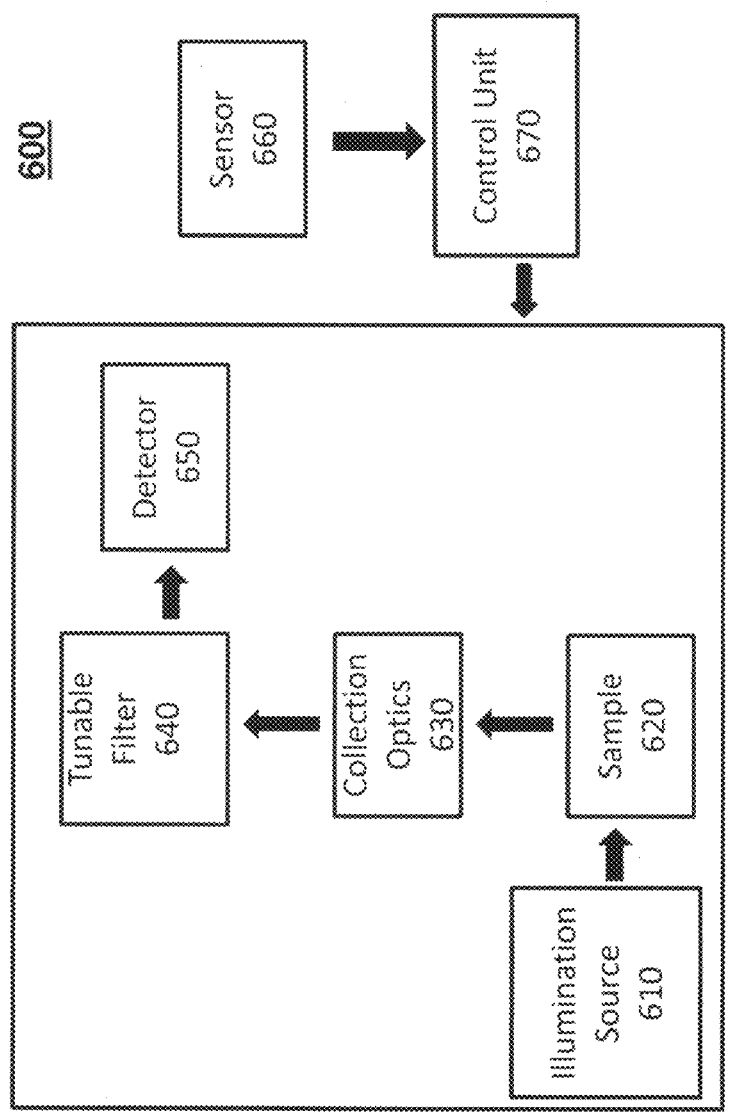
FIG. 6 is illustrative of a system of the present disclosure.

The present disclosure also provides for a system for filter modification based on transmission efficiency, one embodiment of which is illustrated in FIG. 6. The system 600 may comprise an illumination source 610 configured to illuminate a sample 620 to thereby generate a first plurality of interacted photons. The illumination source 610 may comprise an active illumination source (e.g., a laser illumination source), a passive illumination source (e.g., a solar radiation source), and combinations thereof. Collection optics 630 may collect the plurality of interacted photons. The interacted photons may be passed through a tunable filter 640. The tunable filter 640 may be configured so as to sequentially filter said plurality of interacted photons into a plurality of predetermined wavelength bands. The tunable filter 640 may comprise a liquid crystal tunable filter, a multi-conjugate liquid crystal tunable filter, and combinations thereof. The tunable filter 640 may also comprise an acusto-optical tunable filter ("AOTF"), Evans Split-Element liquid crystal tunable filter, Solc liquid crystal tunable filter, Ferroelectric liquid crystal tunable filter, Fabry Perot liquid crystal tunable filter, a hybrid filter, and combinations thereof.

At least one detector 650 may be configured so as to detect said plurality of interacted photons and generate test data representative of said sample. The detector 650 may comprise a detector selected from the group consisting of: a CCD detector, an ICCD detector, an InGaAs detector, an extended range InGaAs detector, an InSb detector, a PtSi detector, a CMOS detector, a MCT detector, an intervac-intensified detector, a microbolometer, and combinations thereof.

The detector 650 may be configured to generate test data which comprises at least one of: a test spectrum, a test image, and combinations thereof. This test image may comprise a hyperspectral test image. A sensor 660 may be configured so as to sense an operating point. This operating point may be received by a control unit 670 from a sensor 660. In one embodiment, the control unit 670 may be configured to search a look-up table based on an operating point (e.g., a temperature, a humidity, an atmospheric pressure) and determine an instrument response correction.

The method 500 and the system 600 hold potential for actively providing an instrument response correction during data acquisition. This active feedback holds potential for enabling accurate and reliable determination of instrument response corrections. This may enable appropriate corrections for fluctuations in tunable filter performance due to environmental factors.

Figure 7B:
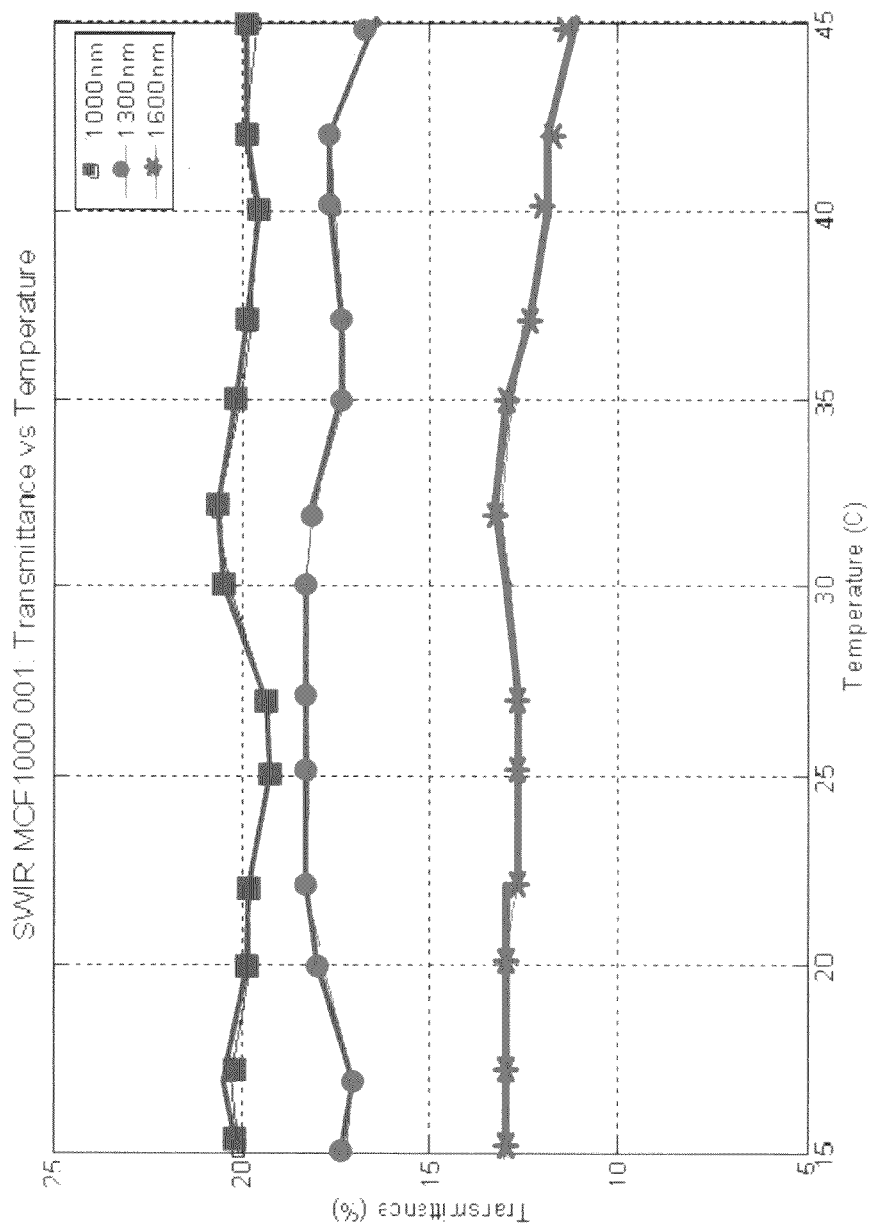
FIG. 7B is a plot representative of an exemplary MCF SWIR filter's transmittance performance with respect to the temperature increment.
Figure 8B:
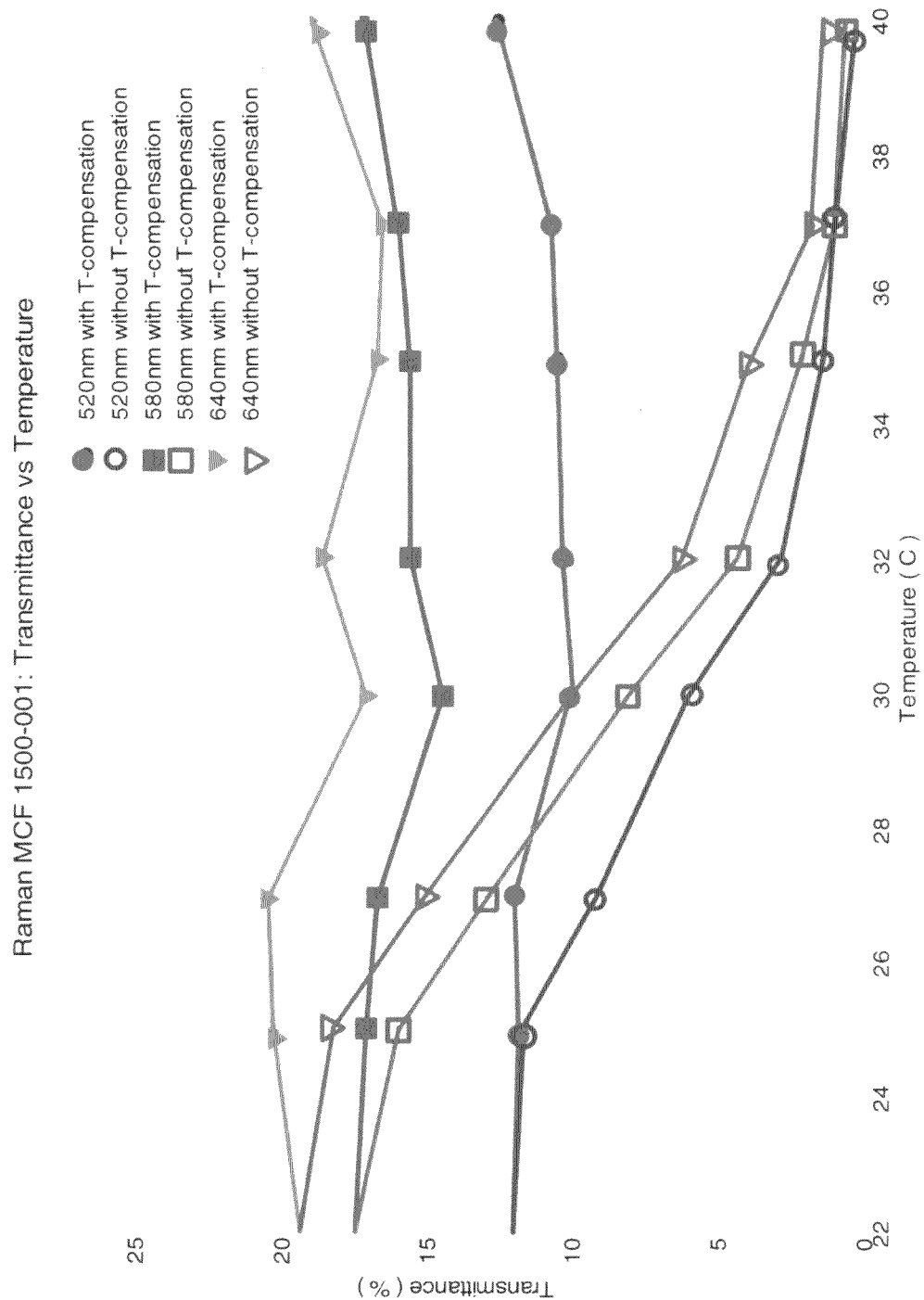
FIG. 8B is a plot representative of an exemplary MCF Raman filter's transmittance performance with respect to the temperature increment.

FIGS. 7A, 7B, 8A, and 8B are provided to illustrate transmission performance with respect to changes in temperature. FIG. 7A provides a data table representative of transmission efficiency for an exemplary SWIR multi-conjugate filter. FIG. 7B is a plot of this transmission v. temperature. FIG. 8A provides a data table representative of efficiency for an exemplary Raman multi-conjugate filter. FIG. 8B is a plot of this transmission v. temperature. It can be seen from the Figures how transmission efficiency is affected by the changes in temperature. The system and method of the present disclosure hold potential for overcoming the challenge of acquiring accurate and reliable transmission information with fluctuations in temperature.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method comprising:
    illuminating a sample to thereby generate a first plurality of interacted photons and a second plurality of interacted photons;
    detecting said first plurality of interacted photons using a dispersive spectrometer to thereby generate at least one reference spectrum representative of said sample;

passing said second plurality of interacted photons through a tunable filter;

detecting said second plurality of interacted photons using an imaging detector to thereby generate at least one hyperspectral test image representative of said sample;

assessing said test image to thereby determine a mean test spectrum wherein said mean test spectrum is representative of the mean intensity of a plurality of pixels in said hyperspectral test image;

comparing said mean test spectrum to said reference spectrum to thereby determine an instrument response correction; and applying said instrument response correction to said hyperspectral test image.

2. The method of claim 1 further comprising masking said test image so as to: include a first plurality of pixels wherein said first portion of pixels comprise pixels sampled by said dispersive spectrometer, and exclude a second plurality of pixels wherein said second portion of pixels comprise pixels not sampled by said dispersive spectrometer.

3. The method of claim 1 further comprising: obtaining a plurality of reference spectra representative of said sample via said dispersive spectrometer, and assessing said plurality of reference spectra to thereby determine a mean reference spectrum representative of said sample.

4. The method of claim 1 wherein said first plurality of interacted photons and said second plurality of interacted photons are detected substantially simultaneously.

5. The method of claim 1 wherein said first plurality of interacted photons and said second plurality of interacted photons are detected sequentially.

6. The method of claim 1 wherein application of said instrument response correction results in an adjusted mean test spectrum associated with said test image, wherein said adjusted mean test spectrum is substantially equal to said reference spectrum.

7. The method of claim 1 wherein at least one of said first plurality of interacted photons and said second plurality of interacted photons are selected from the group consisting of: photons scattered by said sample, photons reflected by said sample, photons absorbed by said sample, photons emitted by said sample, and combinations thereof.

8. The method of claim 1 wherein said reference spectrum comprises at least one Raman spectra.

9. The method of claim 1 wherein said reference spectrum comprises at least one of: a short wave infrared spectra, a near infrared spectra, a mid wave infrared spectra, a long wave infrared spectra, and combinations thereof.

10. The method of claim 1 wherein said sample comprises a biological sample.

11. The method of claim 1 wherein said sample comprises a chemical sample.

12. The method of claim 1 wherein said sample comprises an explosive agent.

13. The method of claim 1 wherein said first plurality of interacted photons are transmitted to said dispersive spectrometer via at least one fiber optic.

14. The method of claim 13 wherein said at least one fiber optic comprises a fiber array spectral translator device.

15. The method of claim 1 wherein said comparing is achieved by applying at least one chemometric technique.

16. The method of claim 1 wherein said hyperspectral test image comprises at least one Raman hyperspectral image.

17. The method of claim 1 wherein said hyperspectral test image comprises a hyperspectral image selected from the group consisting of: a short wave infrared hyperspectral image, a near infrared hyperspectral image, a mid wave infrared hyperspectral image, a long wave infrared hyperspectral image, and combinations thereof.

18. A system comprising:
an illumination source for illuminating a sample to thereby generate a first plurality of interacted photons and a second plurality of interacted photons;
a collection optics for collecting at least one of said first plurality of interacted photons and said second plurality of interacted photons;
a dispersive spectrometer for detecting said first plurality of interacted photons and generating at least one reference spectrum representative of said sample;
at least one fiber optic, wherein a first end of said fiber optic is coupled to said collection optics and said second end is coupled to an entrance slit of said dispersive spectrometer;
a tunable filter for sequentially filtering said second plurality of interacted photons into a plurality of predetermined wavelength bands;
an imaging detector configured so as to detect said second plurality of interacted photons to thereby generate at least one hyperspectral test image representative of said sample; and
at least one processor configured to assess the hyperspectral test image and generate at least one mean test spectra and compare the hyperspectral test image with the reference spectrum.

19. The system of claim 18 further comprising a platform configured to hold said sample.

20. The system of claim 18 wherein said tunable filter comprises a filter selected from the group consisting of: a liquid crystal tunable filter, a multi-conjugate liquid crystal tunable filter, and combinations thereof.

21. The system of claim 18 wherein said imaging detector comprises a Raman hyperspectral imaging detector.

22. The system of claim 18 wherein said imaging detector comprises a hyperspectral imaging detector selected from the group consisting of: a short wave infrared hyperspectral imaging detector, a near infrared hyperspectral imaging detector, a mid wave hyperspectral imaging detector, a long wave hyperspectral imaging detector, and combinations thereof.

23. The system of claim 18 wherein said at least one fiber optic comprises a fiber array spectral translator device.

24. The system of claim 18 further comprising a non-transitory storage medium containing machine readable program code, which, when executed by a processor, causes said processor to perform the following: generate a mean spectrum representative of said hyperspectral test image; compare said mean spectrum to said reference spectra; determine an instrument response correction; and apply said instrument response correction to said hyperspectral test image.

25. A non-transitory data storage medium containing program code, which, when executed by a processor causes said processor to perform the following: illuminate a sample to thereby generate a first plurality of interacted photons and a second plurality of interacted photons; detect said first plurality of interacted photons using a dispersive spectrometer to thereby generate at least one reference spectrum representative of said sample; pass said second plurality of interacted photons through a tunable filter; detect said second plurality of interacted photons using an imaging detector to thereby generate at least one hyperspectral test image representative of said sample; assess said test image to thereby determine a mean test spectrum wherein said mean test spectrum is representative of the mean of the intensity at each pixel in said hyperspectral test image; compare said mean test spectrum to said reference spectrum to thereby determine an instrument response correction; and apply said instrument response correction to said hyperspectral test image.

26. The non-transitory data storage medium of claim 25 which, when executed by a processor further causes said processor to perform the following: obtain a plurality of reference spectra representative of said sample via said dispersive spectrometer, and assess said plurality of reference spectra to thereby determine a mean reference spectra representative of said sample.

27. The non-transitory data storage medium of claim 25 which, when executed by a processor further causes said processor to mask said test image so as to: include a first plurality of pixels wherein said first portion of pixels comprise pixels sampled by said dispersive spectrometer, and exclude a second plurality of pixels wherein said second portion of pixels comprise pixels not sampled by said dispersive spectrometer.

* * * * *